United States Patent
Cheng et al.

(10) Patent No.: US 7,614,316 B2
(45) Date of Patent: Nov. 10, 2009

(54) DISSOLUTION TESTING APPARATUS CALIBRATOR AND METHOD

(75) Inventors: Joel Cheng, North York (CA); Yiu-Chung Lee, Markham (CA); Hitoshi Masui, 40 Kelso Crescent, Maple, Ontario (CA) L6A 2C8; Gabriel Lam, Brampton (CA)

(73) Assignee: Hitoshi Masui, Maple, Ont (CA)

( * ) Notice: Subject to any disclaimer, the term of this patent is extended or adjusted under 35 U.S.C. 154(b) by 0 days.

(21) Appl. No.: 11/788,363

(22) Filed: Apr. 18, 2007

(65) Prior Publication Data
US 2007/0276612 A1    Nov. 29, 2007

(30) Foreign Application Priority Data
Apr. 18, 2006    (CA) ............................ 2544385

(51) Int. Cl.
*G01N 33/00* (2006.01)
(52) U.S. Cl. .................. 73/866; 73/861.08
(58) Field of Classification Search ............... None
See application file for complete search history.

(56) References Cited

OTHER PUBLICATIONS

Foster, T., Brown, W.; USP Dissolution Calibrators: Re-examination and Appraisal; Dissolution Technologies (Feb. 2005), pp. 6-8.
Gray, V., Barat, M., Bhattacharyya, P., Burrnicz, J., Crist, B., et al.; Activities of the USP Project Team on Dissolution Calibration. Dissolution Technologies (Feb. 2005), pp. 35-36.
Kukura, J., Baxter, J.L., Muzzio, F.J; Shear Distribution and Variability in the USP 'Apparatus 2' Under Turbulent Conditions; International Journal of Pharmaceuticals. 279; 2004; pp. 9-17.
Mirza, T.; Mechanical Versus Chemical Dissolution Calibration; Dissolution Technologies 2; Article 1; 2000.

(Continued)

*Primary Examiner*—Robert R Raevis
(74) *Attorney, Agent, or Firm*—David J. Heller; Ridout & Maybee LLP (57) ABSTRACT

A method is provided for probing the effective hydrodynamic flow of a liquid at various positions within a dissolution testing apparatus. The method includes embodiments of an appropriate electrode probe, and methods of generating a signature pattern from the sampled current that may be used to characterise the hydrodynamic flow of the liquid in the apparatus. The signature pattern may be used to validate and qualify the performance of the dissolution apparatus, diagnose problems with dissolution apparatus, predict the initial dissolution rate of a drug, or determine the local flow rate around specific parts of a drug.

8 Claims, 7 Drawing Sheets

OTHER PUBLICATIONS

Glowacki, P.; On the Use of Electrochemical Sensors for Local Velocity Measurement of Viscoelastic Fluids. Wärme- und Stoffübertragung 24, 177-181 (1989).

Deslouis, C., Tribollet, B., Tihon, J.; Near-Wall Turbulence in Drag Reducing Flows Investigated by the Photolithography-Electrochemical Probes. J. Non-Newtonian Fluid Mech. 123 (2004) 141-150.

Deslouis, C., Huet, F., Gil, O., Tribollet, B.; Spectral Analysis of Wall Turbulence with a Bicircular Electrochemical Probe. Experiments in Fluids 16, 97-104 (1993).

Amadi, S.A., Gabe, D.R., Goodenough, M.; An Electrochemical Mass Transport Sensor to Study Agitation in Electroplating Processes. Journal of Applied Electrochemistry 21 (1991) 1114-1119.

Wu, J., Ye, J.; Micro Flow Sensor Based on Two Closely Spaced Amperometric Sensors. Lab Chip, 2005, 5, 1344-1347.

Unwin, P.R., Macpherson, J.V.; New Strategies for Probing Crystal Dissolution Kinetics at the Microscopic Level. Chemical Society Reviews, 1995, 109-119.

Rode, S., Midoux, N., Latifi, M.A., Storck, A., Saatdjian, E.; Hydrodynamics of Liquid Flow in Packed Beds: An Experimental Study Using Electrochemical Shear Rate Sensors. Chemical Engineering Science, vol. 49, No. 6, pp. 889-900, 1994.

Rode, S., Latifi, M.A., Storck, A., Midoux, N.; An Experimental Study of the Frequency Response of Electrochemical Sensors in Nonhomogeneous Flow in Packed Beds. Journal of Applied Electrochemistry 24 (1994) 639-646.

DISSOLUTION TESTING APPARATUS CALIBRATOR AND METHOD

FIELD OF THE INVENTION

The invention relates to an apparatus and method for characterising hydrodynamic flow. In particular, this invention relates to an apparatus and method for characterising hydrodynamic flow in dissolution testing apparatus.

BACKGROUND OF THE INVENTION

In the pharmaceutical industry, it often necessary to ascertain the rate at which a drug in solid form dissolves under certain, well-defined conditions. This process is known as in vitro drug dissolution testing, and is a critical component of pharmaceutical product and process development, as well as manufacturing. Dissolution testing can be used to study the drug release characteristics of a particular dosage form, to evaluate the quality control of the process used to form the drug, and to aid in pharmaceutical formulation development and stability determination. Furthermore, the robustness and uniformity of manufacturing batches are determined using dissolution tests. Consequently, the reproducibility and accuracy of the dissolution tests, as well as the identification of sources that may cause variability between tests, are of the utmost importance.

The United States Pharmacopoeia (USP) compendial 'Apparatus' used for drug dissolution testing are "Apparatus 1" (the basket method), 'Apparatus 2' (the paddle method), 'Apparatus 3' (the reciprocating cylinder), 'Apparatus 4 (the flow-through cell), 'Apparatus 5' (the paddle over disk), 'Apparatus 6' (the cylinder) and 'Apparatus 7' (the reciprocating holder). It is important that the results of the dissolution test are accurate and reproducible. The accuracy and reproducibility of dissolution results is ensured through calibration of the dissolution apparatus. Calibration of a dissolution apparatus demonstrates the suitability of the use of that dissolution apparatus in a dissolution test, and is similar in concept to system suitability determinations for other analytical procedures (Foster, T., Brown, W.; USP Dissolution Calibrators: Re-examination and Appraisal; Dissolution Technologies (February 2005), pp 6-8 (Foster and Brown, 2005) incorporated herein by reference). To assess the suitability of a dissolution apparatus, the USP requires a combination of sufficiently detailed descriptions of the compendial testing apparatus, mechanical calibration, and a demonstration of suitable performance using standard reference materials (chemical calibration). These reference materials are currently in the form of calibrator tablets and include non-disintegrating salicylic acid tablets, and disintegrating prednisone tablets. Ideally, a calibrator tablet should: demonstrate that the entire system is working acceptably, provide an absolute standard for comparing dissolution testing apparatus, and confirm that the system works acceptably as a complement to mechanical calibration (Gray, V.; Barot, M. Bhattacharyya; P., Burmicz, J.; Crist, B., et al.; Activities of the USP Project Team on Dissolution Calibration. Dissolution Technologies (February 2005), pp. 35-36. (Gray et al., 2005) incorporated herein by reference).

Unfortunately, despite the reliance of the USP, the FDA and the industry on dissolution testing, there have been numerous reports in the literature describing high variability and unpredictability of test results, even for the dissolution apparatus calibrator tablets themselves. This variability of test results may result in an apparatus failing a validation test or a batch of drugs being rejected. False-negative calibrator test results lead to time and money being wasted through unnecessary investigation and re-calibration of dissolution apparatus. More concerning is that the false-negative calibrator test results raises doubts in the data obtained from the dissolution apparatus, often leading to additional expense and delay from unnecessary retesting of previous samples. Failed dissolution calibration tests resulted in 14 product recalls in 1999 and 20 product recalls in 2000 (Kukura, J.; Baxter, J. L.; Muzzio, F. J; Shear Distribution and Variability in the USP 'Apparatus 2' Under Turbulent Conditions; International Journal of Pharmaceuticals. 279; 2004; pp. 9-17 (Kukura et al., 2004) incorporated herein by reference). The financial consequences of a dissolution apparatus failing dissolution calibration tests can be significant for a pharmaceutical corporation, necessitating product recalls, costly investigations, potential product delays and even revalidation of the manufacturing process.

There are many sources of the variation of results for dissolution and calibration tests, and it is the role of the calibrator to detect these deviations. One main cause of variation is the hydrodynamics of the liquid within the vicinity of a tablet (either a drug or calibration tablet). Experiments have confirmed that dissolution rates can vary substantially when tablets experience different shear environments due to their locations within the device, and that uneven distribution of the hydrodynamic force is a direct cause of dissolution testing variability (Kukura et al., 2004). Variations in test results may also be caused by the apparatus itself including belt tightness, current surges, shaft wobble, basket imperfections, basket cleanliness, vessel cleanliness, vessel imperfections, vibration, and temperature fluctuations. Variations may further be introduced by the analyst, and may include improper apparatus setup, medium degassing, sample introduction, and sample preparation and filtration (Mirza, T.; Mechanical Versus Chemical Dissolution Calibration; Dissolution Technologies 2; Article 1; 2000. (Mirza, 2000) incorporated herein by reference). A high rate of variability has also been attributed to the calibrator tablets themselves. Thus, there are many different causes for variations of test results that might ultimately result in the failure of a test or apparatus.

There are a number of problems associated with the current methods and tools for the calibration of dissolution apparatus. The salicylic acid calibrator tablets are often found to be fused or chipped in bottles from current lots. These tablets are criticized for alleged insensitivity to perturbational variables related to "Apparatus 1" and 'Apparatus 2' (Foster and Brown, 2005). Furthermore, an argument has been made that there is variability in intrinsic performance of the USP calibrator tablets that has been found to be so great that it often exceeds the variability of the performance of modern dissolution test assemblies (Foster and Brown, 2005). Current dissolution apparatus calibration also interrupts the workflow from a test assembly, requiring a different medium and volume, and often a different apparatus speed for each of 2 separate calibrator tablets. This also means that it will take a long time for the completion of a dissolution calibration run, which will interfere with method development. Lastly, current dissolution calibrator tablets are not diagnostic tools that can determine the cause of failure for a dissolution test. The dissolution of a calibrator tablet is unable to pinpoint the cause of a deviation. A change in dissolution rate can be the culmination of many different effects, including the various causes discussed above. Thus, it is a challenge for the calibration of dissolution apparatus to ensure that the variation seen in multiple dissolution samples represents some intrinsic difference in the units tested and is not the cumulative effect of small differences in the dissolution test environment.

Therefore, there is a need for a method for calibration of dissolution apparatus that is sensitive to vibrations, stable, easy to manufacture in a consistent manner, has minimal toxicity, and can diagnose the cause of the dissolution apparatus failure. There is a further need for a method that improves calibration efficiency and allows for same-day or near-day calibration. There is a further need for a method that minimizes impact on the workflow from a dissolution apparatus. There is a further need for a method that allows for the evaluation of the hydrodynamic environment in the apparatus in order to eliminate this potential source of failure as it is unrelated to product quality. There is a further need for a method that is reproducible, re-usable and less expensive in the long term than the current use of calibrator tablets. There is an additional need for a method of calibration that is applicable to all of the different and accepted apparatus, including "Apparatus 4", for which the USP does not provide calibration guidelines (Gray et al., 2005).

There also is a need for an apparatus to carry out the method for calibration of dissolution apparatus.

BRIEF DESCRIPTION OF THE DRAWINGS

In drawings in which similar references are used in different Figures to denote similar components and which illustrate, by way of example, only a preferred embodiment of the invention.

FIG. 3a is a perspective view of a caplet-shaped, multiple, inlaid-platinum-disk electrode system for determining the relative flow rates at the bottom and end of a caplet;

FIG. 3b is a section view of the caplet of FIG. 3a;

FIG. 3c is a bottom view of the caplet of FIGS. 3a and 3b;

FIG. 4b is an illustration of a Dissolution 'Apparatus 2' with an embodiment of a tape electrode affixed to a side wall of the vessel; and, FIG. 5 is an illustration of a Dissolution 'Apparatus 2' with an embodiment of a system of electrodes on a wall of the vessel.

DETAILED DESCRIPTION OF THE INVENTION

An object of the present invention is to provide a novel method that can be used for the calibration of dissolution apparatus.

Disclosed is a method for characterising hydrodynamic flow of an electrochemically active liquid in a dissolution vessel comprising at least a probe electrode and a reference electrode immersed in the liquid, comprising the steps of: maintaining constant one of the potential at or the current through the probe electrode; collecting data samples representative of the other of the current or the potential not held constant; whereby the data samples characterise the hydrodynamic flow of the liquid in the dissolution vessel. Preferably the method further comprises the step of creating a signature pattern from the data samples. Preferably the signature pattern is compared to a reference signature pattern from a previously collected set of samples.

In an embodiment, the signature pattern is the Fourier Transform of the collected data. In an alternate embodiment the signature pattern is a time average of the collected data. In a further alternate embodiment the signature pattern is a histogram of the collected data.

Also disclosed is an apparatus for characterising hydrodynamic flow of a fluid, the apparatus comprising: a vessel for conducting dissolution tests, a probe electrode embedded in a wall of the vessel, the probe electrode exposed to the interior of the vessel.

Further disclosed is an apparatus for characterising hydrodynamic flow of a fluid, the apparatus comprising a vessel for conducting dissolution tests and a probe electrode on the surface of a wall of the vessel.

Further disclosed is an apparatus for characterising hydrodynamic flow of a fluid around a test object in a dissolution vessel, the apparatus comprising: one or more electrodes embedded in an insulating material, the insulating material shaped to resemble the test object, a non-insulated portion of the one or more electrodes exposed through the surface of the material.

Also disclosed is a system for characterising hydrodynamic flow of a fluid, the system comprising: a probe electrode, a reference electrode and a counter electrode; the electrodes connected to a data sample collection means; the data sample collection means fixing one of the potential at the probe electrode or the current through the probe electrode; the data sample collection means collecting and storing data samples representative of the other of the potential or the current not fixed.

Further disclosed is a tablet-shaped probe for characterising hydrodynamic flow of a fluid, the probe comprising a tablet-sized tube, a magnet fixed in an end of the tube and an electrode embedded in epoxy at an alternate end of the tube.

Generally, the invention relates to providing an inert electrode that is held at an appropriate, constant potential (potentiostatic mode) to cause a mass-transport-limited electrochemical reaction to occur when immersed in an electrochemically active solution contained within a dissolution vessel or cell. The transfer of electrons between the electrode and the electroactive molecules/ions of the solution generates an electric current whose magnitude depends on the rate at which the molecules are transported to the electrode, and this in turn, depends on the flow rate of solution past the electrode. Alternatively, a constant electrochemical current can be made to flow by adjusting the potential of the electrode (galvanostatic mode), and the magnitude of the potential can be measured as an indicator of the flow rate of the solution past the electrode.

The electric current (in potentiostatic mode) or electrode potential (in galvanostatic mode) fluctuates with time according to the hydrodynamics within the vessel or cell, the fluctations being specific to the vessel or cell. Factors which affect the flow of the liquid, such as mechanical variances in the dissolution apparatus, will affect the fluctuations. By sampling the fluctuating current or potential, and applying mathematical analytical techniques to the samples, it is possible to identify a signature pattern from the sampled data and observe changes in the physical setup of the apparatus by changes in the signature pattern. The electrode may be formed in various shapes depending on the application, examples of which are herein described.

In a preferred embodiment, a three electrode arrangement is used with a probe electrode, a reference electrode and a counter electrode. The advantage of using a three electrode arrangement is that the activity of the reference electrode is reduced significantly as it is no longer being used as a sacrificial electrode. While this embodiment is preferred due to its stability and all examples described below assume use of a three electrode arrangement, a two electrode arrangement would also be suitable to characterise the hydrodynamic flow of a dissolution apparatus. A two electrode arrangement could be used, for instance, where the reference electrode is discarded after it has been sacrificed in the reaction, and a new reference electrode is introduced for additional tests. Alternatively, an electrochemically active electrode, such as copper, may be used instead of an inert probe electrode; however, this is not preferred, since it too, will be consumed and have to be replaced.

Figure 1:
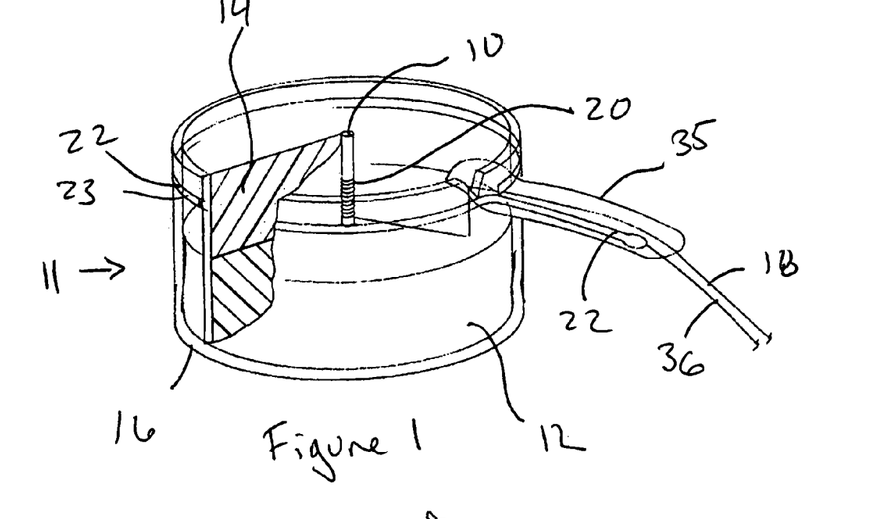
FIG. 1 is a perspective view of a tablet-shaped, inlaid-platinum-disk electrode.
Figure 2:
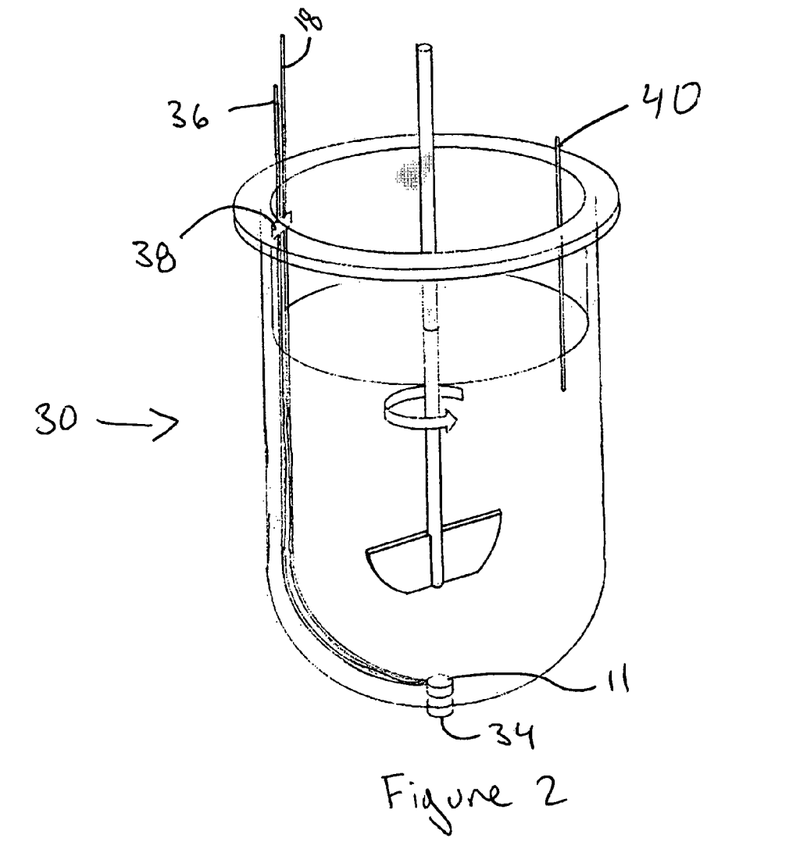
FIG. 2 is a perspective view of the placement of a tablet-shaped, inlaid-platinum-disk electrode in the vessel of a Dissolution 'Apparatus 2'.

One preferred embodiment of the method involves an inlaid-platinum-disk probe electrode 11, as shown in FIG. 1, used in conjunction with dissolution 'Apparatus 2', 'Apparatus 4', or 'Apparatus 5'. The probe electrode 11 may be conveniently formed by embedding a short segment of platinum wire 10 coaxially in a tablet-shaped epoxy cylinder 14, and sanding and polishing flat one end of the cylinder such that an inlaid disk of platinum is exposed, to comprise a section of a tablet-shaped probe. The tablet-shaped probe 11 may preferably be completed by combining the epoxy cylinder 14 with a tablet-shaped magnet 12 that makes up the remaining section of the tablet-shaped probe 11. The addition of a retaining magnet 34 as shown in FIG. 2 provides a convenient means for positioning the probe 11 in a vessel 30, and maintaining the position of the probe 11 throughout a test. As will be appreciated, while it is not necessary for the magnet 12 to be tablet-shaped, employing a tablet-shaped magnet 12 provides a convenient and simple assembly to create a tablet-shaped probe 11.

In a preferred method of manufacture, a tablet-sized tube 16 provides a convenient mould for setting the epoxy into a tablet-shaped epoxy cylinder 14. In a preferred embodiment, the tube 16 is comprised of polycarbonate. Conveniently, the magnet 12 may be aligned with the epoxy cylinder 14 by inserting into the tablet-sized tube 16. The magnet 12 may be electrically isolated from the epoxy cylinder 14 and wire 10 by providing an insulating barrier between the magnet 12 and the epoxy cylinder 14. In one embodiment the insulating barrier is a non-conductive adhesive tape shaped and sized to insulate the magnet 12 from the epoxy cylinder 14. Alternatively, the insulating barrier may be a coating applied to the magnet 12 or epoxy cylinder 14 before assembly to comprise the tablet-shaped probe 11.

Electrical contact may preferably be made to the platinum wire 10 via a thin insulated copper wire 18 stripped at both ends, with one end 20 of the wire 18 wrapped around the platinum wire 10 and embedded in the epoxy cylinder 14. Other methods may be used to form an electrical contact including fusing or pressing a wire 18 to the platinum wire 10.

A silver wire 22, wrapped around the periphery of the tube 16 may serve as the reference electrode 23. Alternatively, the tube 16 may be provided with a silver coating to comprise the reference electrode 23. In an alternate embodiment, not shown, an epoxy cylinder 14 may be formed in a mould, avoiding use of the tube 16. In this alternate embodiment without a tube 16, the silver wire 22 or silver coating may be provided on the epoxy cylinder 14.

Electrical contact may be made to the silver wire 22 via a thin insulated copper wire 36 stripped at both ends, with one end soldered to the silver wire 22 and the joint insulated by an epoxy coating 35. A stainless steel wire immersed to a depth of 1 cm in the dissolution vessel 30 ('Apparatus 2' or 'Apparatus 5'), as shown in FIG. 2, or a disk of stainless steel mesh, positioned at the top of the flow-through cell ('Apparatus 4'), may serve as a counter electrode 40. Electrical contact to the counter electrode 40 may be made via another thin, insulated copper wire stripped at both ends. The free end of each wire may be led out of the vessel 30 or cell and around any gaskets to make connections with the potentiostat/amperometric detector in the usual three-electrode-cell configuration.

Figure 4A:
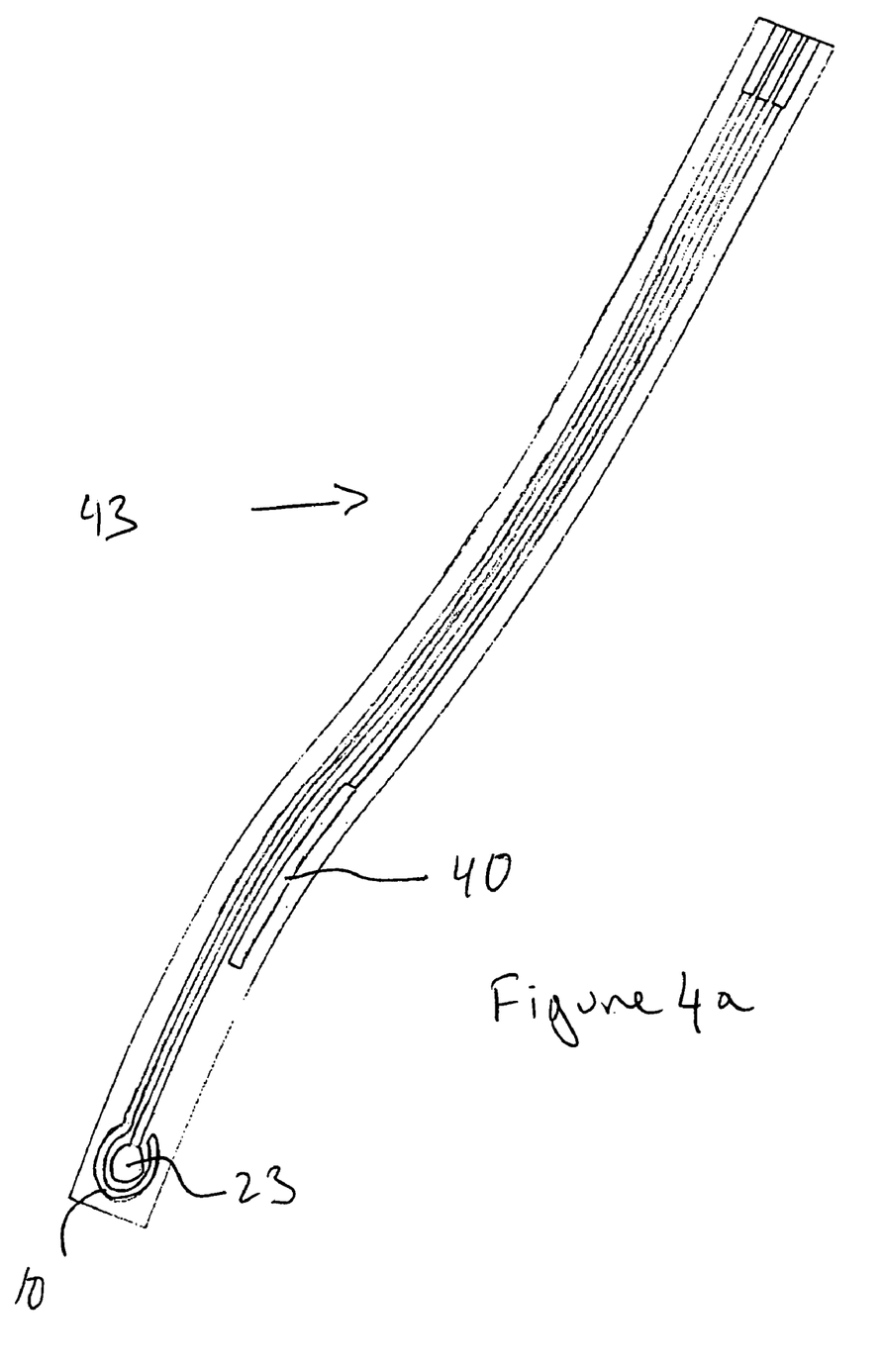
FIG. 4a is an illustration of an embodiment of a tape electrode.

Alternatively, as illustrated in FIG. 4a the probe electrode 10, reference electrode 23 and counter electrode 40 may comprise lithographed, or otherwise formed, metal patterns on a tape 43. Preferably, as illustrated in FIG. 4b, tape 43 further comprises an adhesive side so that the tape 43 may be applied to an inner surface of the vessel 30.

Figures 4B, 5:
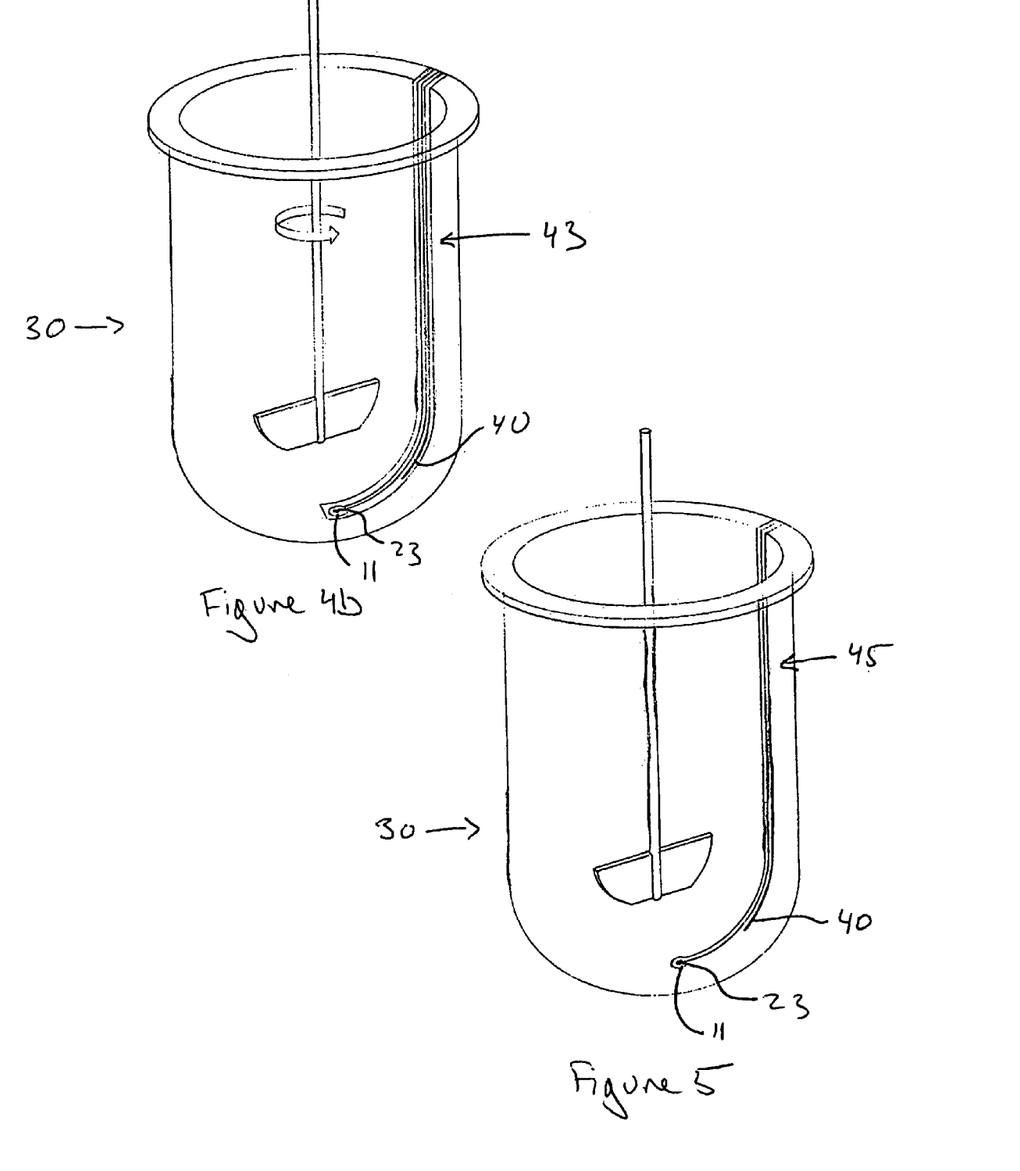

In an alternate embodiment illustrated in FIG. 5, a vessel 30 may comprise a measurement device by providing a lithographed, or otherwise formed, metal pattern 45 on the inner surface of the vessel 30. The metal pattern 45 comprises the probe electrode 10, reference electrode 23 and counter electrode 40 in a fixed arrangement on an inner surface of the vessel.

In an alternate embodiment, not shown, the probe electrode 10, reference electrode 23 and counter electrode 40 may comprise electrodes exposed through an inner wall of the vessel 30, where the electrodes are inserted through holes in the wall of the vessel 30, or cast or formed into the wall of the vessel 30, with electrical leads connected to the electrodes from outside the vessel.

The dissolution vessel 30 may be filled with an electrochemically active solution. It has been found that a liquid containing approximately 0.1 M of an electrochemically-inactive supporting electrolyte (e.g. aqueous potassium chloride) and approximately 1 mM of an electrochemically-active solute (e.g. aqueous sodium iodide) provides sufficient electrochemical activity to carry out the method. A potential applied to the platinum electrode causes a mass-transport-limited electrochemical reaction (for sodium iodide as the electrochemically-active solute, typically about 1.0 V versus the potential of the silver electrode is applied). The current generated by the electrochemical reaction may be sampled in time to yield amperometric data.

Surprisingly, it has been found that the amperometric data may be analyzed by mathematical methods to draw out signature patterns from the amperometric data that characterise the hydrodynamic flow in a dissolution apparatus. These signature patterns may be interpreted to describe a particular aspect of the hydrodynamic flow at the electrode within the dissolution apparatus such as the average hydrodynamic flow. For example, a useful signature pattern may comprise the average current. By comparing the average current measured at one time to the average current measured at another time, one may determine if the apparatus is exhibiting similar hydrodynamic flow. Variations in the physical setup of the apparatus, such as belt tightness, current surges, shaft wobble, vessel imperfections, vessel tilt, and vibration, will lead to variations in the hydrodynamic flow and may be identified by a change in the signature pattern.

The signature pattern provides a metric that may be used to validate and qualify the performance of the dissolution vessel or cell, by comparing a standard or reference signature pattern to non-standard patterns. Additionally, if a change in the hydrodynamic flow is detected, the type of variation in the signature pattern may be used to diagnose the problem and identify the source of the variation. For example, spikes in the current over time may indicate that the vessel was bumped during the calibration run. Other identified patterns may indicate that there is a wobble in the shaft, that vibrations may have occurred, or that the vessel has been tilted. By reusing the same electrode for a particular dissolution apparatus, any variations that may result from the calibrator itself are removed.

In a further preferred embodiment, the initial dissolution rate of a drug may be determined by constructing an electrode from an electrically-conductive material (for example, graphite composite or metal-plated substrate) in the shape of the drug. Electrical contact may be made to the electrode via a thin insulated copper wire stripped at both ends, with one end of the wire embedded within the electrode. A thin insulated silver wire, also stripped at both ends, runs alongside the copper wire and serves as the reference electrode. A wire or mesh of stainless steel may serve as a counter electrode. Electrical contact to the stainless steel is made via another thin, insulated copper wire stripped at both ends. The free end of each wire may be led out of the vessel or cell and around any gaskets to make connections with the potentiostat/amperometric detector in the usual three-electrode-cell configuration. The dissolution vessel may be filled with a solution and a potential may be applied to the electrode for collecting amperometric data, as described above. The measured electric current is indicative of the drug's initial dissolution rate, averaged over the surface of the drug. In this way, the initial dissolution rate of various shapes and sizes of drug forms can be studied by constructing the electrode to mimic the drug form of interest.

In a further preferred embodiment, a platinum-bead probe electrode may be used to determine the hydrodynamic flow rate at distinct points throughout the vessel 30. A platinum bead electrode may be formed, for instance, by melting the end of a 0.10 mm diameter platinum wire in a flame, typically resulting in a bead electrode diameter of about 0.5-1.0 mm. The remaining wire may be electrically insulated with lacquer to serve as an electrical lead attached to the bead. After filling the vessel 30 with an electrochemically active liquid, current or voltage data may be collected. The sampled data indicates the local hydrodynamic flow in the vicinity of the platinum bead electrode. The bead probe electrode may be moved to alternate locations within the vessel 30 and data collected at each new location. By repeating the experiment for multiple locations within a vessel 30, it may be possible to map the flow rate within the vessel 30. Mapping the flow rate throughout a vessel 30 may be useful in designing dissolution equipment, or developing protocols to ensure reproducible operation of existing dissolution equipment.

Figures 3A, 3B, 3C:
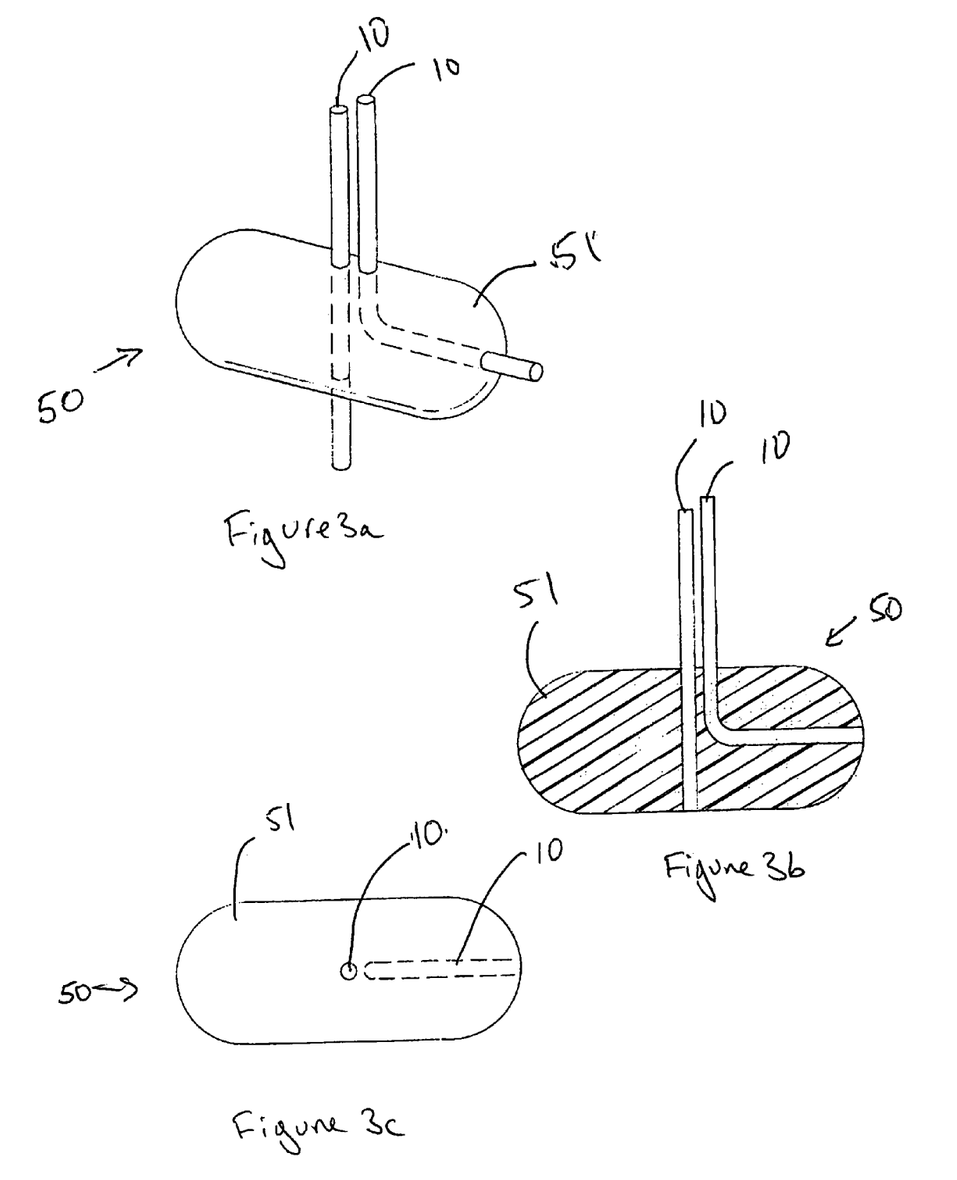

In an additional preferred embodiment illustrated in FIGS. 3a, 3b and 3c and described further below, one or more inlaid-platinum-disk probe electrodes may be embedded in an electrically insulating "dummy" tablet or capsule 50 by casting epoxy 51 in a mould around thin platinum wires 10. As illustrated in FIGS. 3b and 3c, the wires 10 may be cut and polished flush with the surface of the epoxy 51, forming embedded platinum disk electrodes. The resultant one or more electrodes may be used to collect current or voltage data to investigate how the flow rate at the location of the one or more electrodes on the surface of capsule 50 are affected by the capsule's 50 shape. This embodiment may assist in determining the shape of future drugs; if for example, it is found that the ends of a particular drug form dissolve too fast.

In an additional preferred embodiment of the method, an inlaid-platinum-disk probe electrode may be constructed such that it is embedded within, on or through a wall of the dissolution vessel. Amperometric data collected from this arrangement may be used to investigate the flow rate at the position of the embedded electrode and to generate a signature pattern for a properly operating dissolution apparatus. In this case, the probe electrode would be part of a self-checking dissolution apparatus, wherein the data collected in later tests could be compared to the original signature pattern to ensure that the apparatus was operating correctly. Embedding the electrode in the wall of the vessel ensures that the electrode does not perturb the hydrodynamics of the vessel and ensures that the electrode is in the same position at all times.

In another preferred embodiment of the method, an inlaid-platinum-disk probe electrode may be constructed, which contains a small battery and integrated circuitry. The integrated circuit may serve both as a potentiostat/galvanostat and a transmitter, thereby, making the system wireless. Such a device makes the method much simpler to use and applicable to dissolution apparatus that operate by moving the drug delivery system through the dissolution medium; for example, 'Apparatus 1', 'Apparatus 3', 'Apparatus 6', and 'Apparatus 7'. The sampled data may then be transmitted to a receiver external to the vessel.

The above preferred embodiments could also be employed to achieve hydrodynamically equivalent conditions between different apparatus. For example, a tablet may be made to dissolve at equivalent rates in both 'Apparatus 1' and 'Apparatus 4' under a specified set of conditions. This would allow dissolution data collected on one apparatus to be quantitatively compared with those collected on a different apparatus. A person skilled in the art will recognize that data collected from an electrode immersed in an electrochemically active solution contained within any vessel can be analyzed to probe the hydrodynamic flow at various positions within the vessel, and that this may have a wide range of different applications. Furthermore, a person skilled in the art will recognize that the electrode used in this method is used by way of example only and in no way should be taken as limiting the scope of the invention. As will be appreciated, suitable electrodes may be constructed from many different materials and in many different shapes, and that the electrochemically active solution contained within the vessel may contain a wide range of electrolytes and electrochemically active solutes.

Generating a Signature Pattern for a Dissolution 'Apparatus 2'

In a first exemplary embodiment, a tablet-shaped electrode may be formed from a cylindrical neodymium magnet 12 (0.80 mm dia., 3.0 mm height) inserted into a cylindrical tube 16 of polycarbonate plastic (0.806 mm i.d., 10.07 mm o.d., 6.0 mm height) such that one end of the magnet 34 is flush with the rim of the plastic tube 16, as shown in FIG. 1.

The end of the magnet 12 facing the inside of the tube 16 is electrically insulated with a circular piece of clear adhesive tape of the same diameter. The stripped end of wire 18 (32 gauge, 40 cm length) is tightly wrapped around a segment of platinum wire 10 (0.5 mm dia. 3.0 mm length) starting from the middle of the segment to one end. A V-shaped notch 8 (1 mm deep) may be filed into the polycarbonate tube 16 on the rim that is not flush with the magnet 12. The platinum wire 10 is positioned coaxially in the polycarbonate tube 16 with the wire-wrapped end toward the adhesive tape. The magnet wire is led through the notch and epoxy is poured around the platinum wire 10 to the brim of the polycarbonate cylinder. The epoxy is allowed to cure for 24 hours and is sanded until an inlaid-platinum-disk is exposed. Fine sandpaper and polish may then used to form a smooth finish. A segment of silver wire 22 (0.5 mm dia., 34 mm length) is formed into a tightly fitting ring around the circumference of the polycarbonate tube 16, and the excess wire is bent perpendicularly outward like a panhandle. The silver ring is positioned near the rim such that the "panhandle" is close to the V-notch. Wire (32 gauge, 40 cm length) is soldered to the "panhandle," and epoxy is used to insulate the connection and secure the silver wire 22 in place near the V-notch. After curing the epoxy for 24 hours, the electrode assembly is complete.

The tablet electrode may be employed within a dissolution vessel as illustrated in FIG. 2. As illustrated, the electrode may be positioned at the bottom of a dissolution vessel 30, coaxially aligned with the paddle 32 with the platinum disk 11 facing upward. The assembly is held in position by utilizing the attraction of a retaining magnet 34, placed on the outside of the vessel 30. Once the electrode assembly and vessel 30 are inserted into the dissolution apparatus (SOTAX AT-7 Smart, for example), the magnet wires 18, 36 are led upward along the inner wall of the vessel 30 and over the rim. A small piece of electrical tape 38 is used to secure the magnet wires 18, 36 near the rim of the vessel 30.

According to a preferred experimental arrangement, the dissolution vessel 30 is filled with 900 mL of an aqueous solution, preferrably containing 0.1M potassium chloride and 1.0 mM sodium iodide. The magnet wire 36 attached to the platinum electrode 11 is connected to the working electrode input of a potentiostat and the magnet wire 18 attached to the silver ring is connected to the reference input. A stainless steel wire, is submerged to a depth of 1 cm in the aqueous solution contained within the vessel. A copper wire, stripped at both ends, may be used to electrically connect the stainless steel wire to the counter electrode input of the potentiostat. Cyclic voltammetry is performed on the quiescent aqueous solution from 0.0 to 1.0 volts at a scan rate of 100 mV/sec to determine the peak potential of the iodide oxidation wave. The electrode is then poised at a potential that is 150 mV positive of the oxidation wave peak. The paddle 32 of the dissolution apparatus is rotated at 100 rpm and amperometric data are collected (typically, 16 samples per second for 256 seconds) and digitally stored. For a properly operating dissolution apparatus, this amperometric data becomes its reference signature pattern, as shown in FIG. 6 (Effect of Rotation Rate on Signature Pattern).

Figure 6:
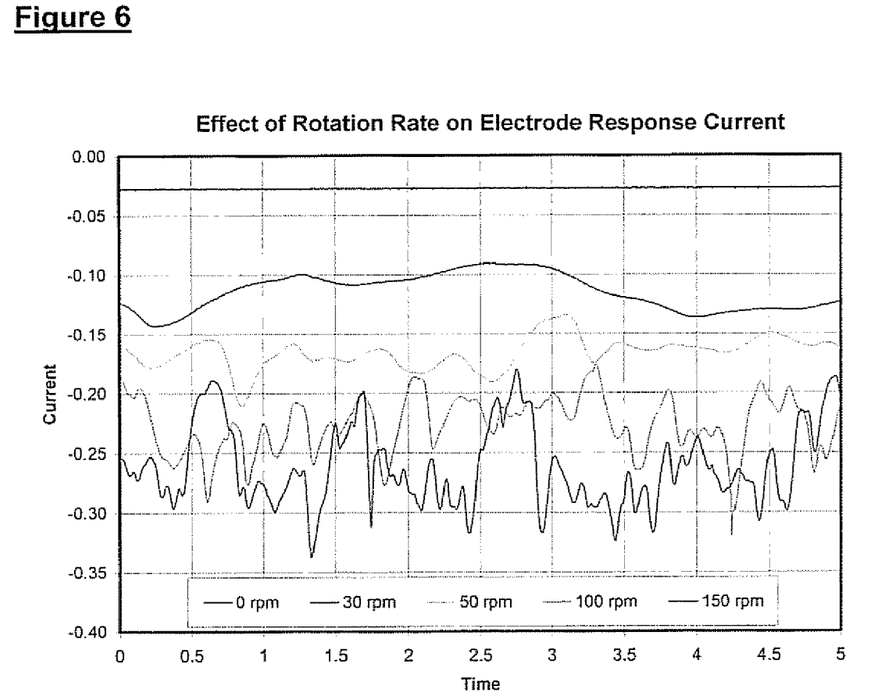
FIG. 6 is a graph showing the effect of rotation rate on the electrode response current.

The graph of FIG. 6 shows the effect of the paddle rotation rate on the electrode response current (signature pattern). The data were generated using a tablet-shaped, inlaid-platinum-disk electrode, immersed in a solution containing 1.0 mM sodium iodide and 0.1 M potassium chloride contained within a Dissolution 'Apparatus 2' vessel. A potential of 1.0 V was applied to the electrode, referenced against a silver wire ring surrounding the inlaid-platinum-disk. Data were collected at a sample rate of 4 samples per second for a total acquisition time of 256 seconds, but only a 5 second portion of the data is shown.

The data may be further analyzed by fast Fourier transformation, current distribution histograms, and statistical methods, yielding the mean, mode, and standard deviation of the current to create a signature pattern.

Validation and Qualification of the Performance of a Dissolution 'Apparatus 2'

In an alternate exemplary embodiment, the method may be used to validate and qualify the performance of a dissolution apparatus, such as a Dissolution 'Apparatus 2'. In this embodiment, a reference signature pattern for the hydrodynamic flow at a tablet-shaped, inlaid-platinum-disk electrode within a properly operating dissolution apparatus (SOTAX AT-7 Smart, for example) may be acquired and stored, as described above to provide a reference signature pattern. After several months, the same electrode may then be used to validate and qualify the performance of the same apparatus.

The apparatus is validated re-collecting the amperometric data, and comparing at least one signature pattern from the re-collected data to the reference signature pattern stored previously. If any significant variations are detected between the signature patterns, it can be assumed that there is some sort of perturbation within the vessel or the system that is causing the variation. Thus, this instrument is no longer considered calibrated, and the source of the variation must be diagnosed and fixed in order for the dissolution apparatus to be validated and qualified.

Figure 7:
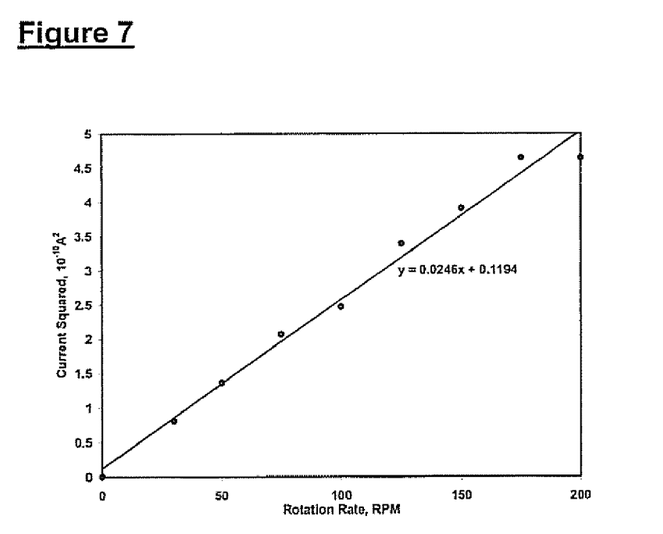
FIG. 7 is a graph showing the square of the average current vs. rotation rate.

It has surprisingly been found that signature patterns may be conveniently compared when the mean of the current squared is used as the signature pattern. The mean of the current squared is proportional to the average flow rate, as shown in FIG. 7. If this value deviates from that of the standard or reference signature pattern by more than ±5%, for instance, then the apparatus fails the validation test. Other indicators may include the degree of skewing of, and any anomalous outliers on, the current distribution histogram, and significant dispersion of frequencies in the power spectrum of the current. These are discussed in more detail below.

The graph of FIG. 7 shows that the square of the average electrode current in a Dissolution 'Apparatus 2' is linearly related to the paddle rotation rate. The data shown in FIG. 7 was collected using a tablet-shaped, inlaid-platinum-disk electrode, immersed in a solution of 1.0 mM sodium iodide and 0.1 M potassium chloride contained within a Dissolution 'Apparatus 2' vessel.

Using a Tablet-Shaped, Inlaid-Platinum-Disk Electrode to Diagnose Problems with a Dissolution 'Apparatus 2'

In a further exemplary method, a signature pattern of the current at a tablet-shaped, inlaid-platinum-disk electrode within a properly operating dissolution apparatus would have been previously generated, as described above. After several months, the same electrode could then be used to validate and qualify the performance of the dissolution apparatus, as described above. If a significant difference between the new pattern and the signature pattern is identified, there must be some type of perturbation affecting the dissolution apparatus. The cause of the perturbation may be deduced by examining the new amperometric data, possibly by generating additional signature patterns. For example, a dissolution vessel that is tilted so that it is no longer coaxial with the paddle will produce a higher mean current than a properly aligned vessel. Furthermore, the Fourier transformed power spectrum of the current will show a dispersion of many frequencies compared to that of a properly aligned vessel, which shows a dominant peak at about 0.36 times the paddle rotation frequency, as shown in FIG. 8.

Figure 8:
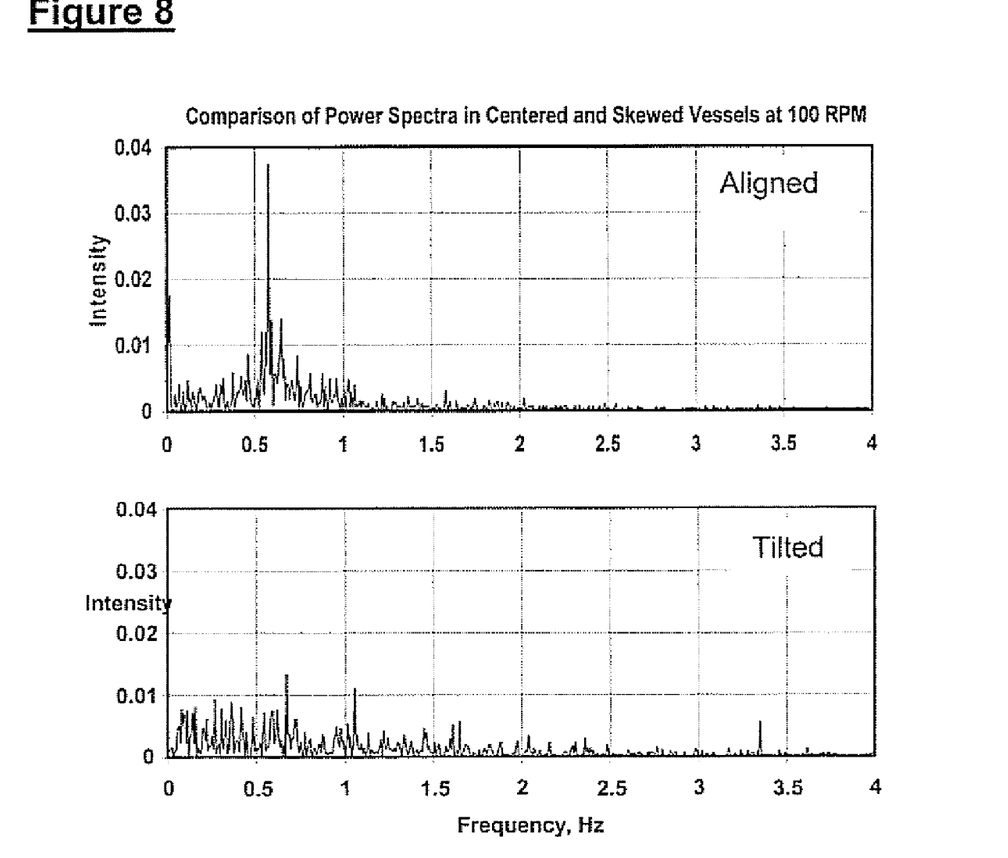
FIG. 8 is a graph comparing power spectra in a properly aligned vessel and a tilted vessel.

The graph of FIG. 8 shows the Fourier transform power spectrum of the signature pattern of a Dissolution 'Apparatus 2'. Fourier-transformed power spectra of the amperometric data were obtained from a properly positioned vessel and an off-center vessel, tilted 1.8° off the paddle axis. The aligned vessel shows a dominant peak at 0.58 Hz, which is 0.36 times the paddle rotation frequency of 1.67 Hz. The tilted vessel, however, shows a dispersion of frequencies, including a fairly prominent peak at twice the paddle rotation frequency. The data were generated using a tablet-shaped, inlaid-platinum-disk probe electrode, held at 1.0 V versus a silver-wire reference electrode, immersed in a solution of 1.0 mM sodium iodide and 0.1 M potassium chloride, which was contained within a Dissolution 'Apparatus 2' vessel.

In a further embodiment of the method, a paddle that is rotating either too fast or too slow may be diagnosed from the mean current, which increases proportionately with the square root of the rotation rate. Also, the frequency of the dominant peak in the power spectrum is proportional to the rotation rate.

Figure 9:
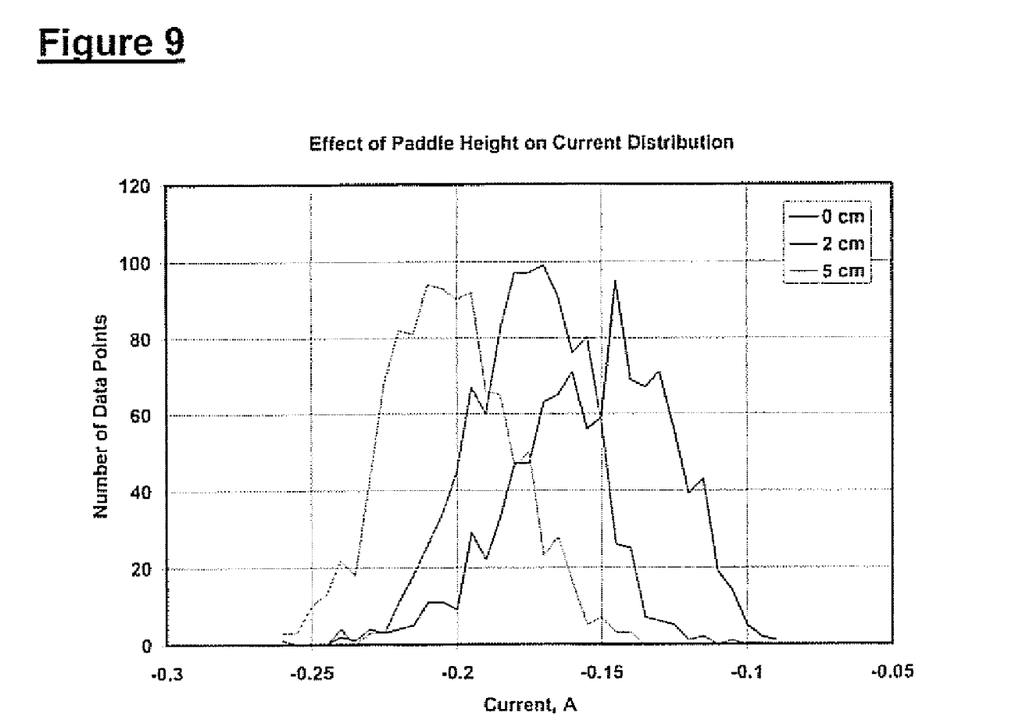
FIG. 9 is a histogram showing the effect of paddle height on current distribution.

In a further embodiment of the method, a paddle that is raised too far from the bottom of the dissolution vessel has an elevated mean current and a histogram that has a symmetrical bell-shaped distribution, whereas a properly raised paddle will have a lower mean current and a histogram that has a skewed bell-shaped distribution, as shown in the histogram of FIG. 9.

The histogram of FIG. 9 shows a distribution of current data as a function of paddle height. The data were obtained using a tablet-shaped, inlaid-platinum-disk probe electrode, centered at the bottom of the vessel of a Dissolution 'Apparatus 2', and held at 1.0 V versus a silver reference electrode. A solution of 1.0 mM sodium iodide and 0.1 M potassium chloride was contained within the vessel, and the paddle was rotated at 100 rpm. Data samples were collected at 2 samples per second for 256 seconds. The paddle height displayed in the legend is relative to the USP-accepted height of 2.5 cm from the bottom of the vessel.

Using a Tablet Shaped Electrode to Determine the Relative Dissolution Rates at Various Locations on a Caplet in 'Apparatus 2'

In an alternate exemplary embodiment of an electrode, several inlaid-platinum-disk probe electrodes may be embedded in an electrically insulating, epoxy caplet 50 by casting the epoxy in a mould around thin platinum wires. As shown in FIGS. 4a to 4c, a caplet-shaped, multiple inlaid-platinum-disk electrode system may be constructed for determining the liquid flow rates at the bottom and end of a caplet 50. As illustrated in FIG. 4a, the caplet may preferably be constructed by sealing platinum wires 10 in an epoxy caplet 50. As illustrated in top and cross-sectional views, FIGS. 4b and 4c, the wires 10 may be cut and polished flush with the surface of the epoxy, forming embedded, platinum-disk electrodes.

According to a preferred experimental arrangement, the electrode assembly may then be placed into a dissolution vessel filled with an aqueous solution of 0.1 M potassium chloride and 1.0 mM sodium iodide and a potential of about 1.0 V may be applied to the platinum-disk electrodes relative to a silver reference electrode.

Each electrode may then be connected to an independent current measuring system, and the resulting amperometric data collected using a multiplexer, sampling the current at each electrode at a rate sufficiently fast to accurately follow the current fluctuations. The acquisition time should be enough to discern patterns. The resultant data may then be stored and the mean squared current calculated at each electrode to investigate how the relative flow rates at specific points on the tablet's surface are affected by the tablet's shape. Fourier transformation of the current data generates a signature pattern that provides information regarding the frequency of flow rate fluctuations at each electrode, while histograms show the distribution of flow rates over time.

Various embodiments of the present invention having been thus described in detail by way of example, it will be apparent to those skilled in the art that variations and modifications may be made without departing from the invention. The invention includes all such variations and modifications as fall within the scope of the appended claims.

We claim:

1. A method for characterising hydrodynamic flow of an electrochemically active liquid in a dissolution vessel comprising at least a probe electrode and a reference electrode immersed in the liquid, comprising the steps of:
   fixing one of the potential at or the current through the probe electrode;
   collecting data samples representative of the other of the current or the potential not held constant;
   creating a signature pattern based on the data samples to characterise the hydrodynamic flow of the liquid in the dissolution vessel and wherein the signature pattern is used to characterise a dissolution apparatus.

2. The method of claim 1 further comprising collecting a further set of data samples and comparing the further data samples to said signature pattern.

3. The method of claim 2 wherein the signature pattern is selected from the group of: a Fourier Transform of the collected data, a time average of the collected data, or a histogram of the collected data.

4. The method of claim 2 wherein the comparison is used to diagnose a fault in the dissolution apparatus.

5. The method of claim 1 wherein said method characterizes hydrodynamic flow about a test object.

6. The method of claim 1 further comprising using the data samples to predict an initial dissolution rate of a drug.

7. The method of claim 1 further comprising using the data samples to determine a local flow rate around specific parts of a drug.

8. The method of claim 1 wherein said vessel further comprises a counter electrode immersed in the liquid, and said method further comprises the step of applying a voltage across the probe electrode and the counter electrode such that the potential of the probe electrode is constant with respect to the reference electrode and sufficient to cause mass-transport limited oxidation or reduction of the electrochemically active liquid.

* * * * *